(12) United States Patent
Kumar et al.

(10) Patent No.: US 10,710,943 B1
(45) Date of Patent: Jul. 14, 2020

(54) PROCESSES FOR ISOMERIZING HYDROCARBONS

(71) Applicant: UOP LLC, Des Plaines, IL (US)

(72) Inventors: Manoj Kumar, Haryana (IN); David James Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/263,733

(22) Filed: Jan. 31, 2019

(51) Int. Cl.
| | |
|---|---|
| C07C 5/13 | (2006.01) |
| C10G 35/04 | (2006.01) |
| C07C 5/22 | (2006.01) |
| B01D 53/68 | (2006.01) |
| C07C 9/10 | (2006.01) |
| C07C 9/14 | (2006.01) |

(52) U.S. Cl.
CPC ............... C07C 5/13 (2013.01); B01D 53/68 (2013.01); C07C 5/2206 (2013.01); C10G 35/04 (2013.01); B01D 2257/2045 (2013.01); C07C 9/10 (2013.01); C07C 9/14 (2013.01)

(58) Field of Classification Search
None
See application file for complete search history.

(56) References Cited

U.S. PATENT DOCUMENTS

| | | | |
|---|---|---|---|
| 2,454,149 A | 11/1948 | Franklin et al. | |
| 2,786,086 A | 12/1953 | Gitterman | |
| 2,946,736 A | 7/1960 | Muffat et al. | |
| 3,156,738 A | 11/1964 | Reveal et al. | |
| 3,227,776 A | 1/1966 | Ross | |
| 3,271,467 A | 9/1966 | Nakayama | |
| 4,275,257 A | 6/1981 | Hutson, Jr. | |
| 7,223,898 B2* | 5/2007 | Rice | C07C 5/2791 585/734 |
| 7,638,665 B2 | 12/2009 | Shecterle | |
| 9,745,232 B2 | 8/2017 | Pigourier et al. | |
| 2008/0286173 A1 | 11/2008 | Shecterle | |
| 2013/0096356 A1 | 4/2013 | Bharuka et al. | |
| 2016/0107954 A1 | 4/2016 | Pigourier et al. | |

FOREIGN PATENT DOCUMENTS

| | | |
|---|---|---|
| GB | 610009 | 10/1948 |
| RU | 2364582 C2 | 4/2009 |
| RU | 2604735 C1 | 12/2016 |

OTHER PUBLICATIONS

U.S. Appl. No. 15/813,057, filed Nov. 14, 2017.

* cited by examiner

Primary Examiner — Derek N Mueller

(57) ABSTRACT

Processes and apparatus for isomerizing hydrocarbons are provided. The process comprises isomerizing at least a portion of the hydrocarbon feed stream comprising at least one of C4 to C7 hydrocarbons in the presence of an isomerization catalyst and hydrogen under isomerization conditions to produce an isomerized stream. The isomerized stream is stabilized in a stabilizer to provide a stabilizer off-gas stream comprising chlorides and a liquid isomerate stream. At least a portion of the stabilizer off-gas stream is contacted with a dried feed stream to remove chlorides from the stabilizer off-gas stream. The dried feed stream is not cooled before absorbing the chlorides. A portion of the dried feed stream may bypass the absorbing section. A chiller is disposed on top of the vessel with the absorbing section.

19 Claims, 1 Drawing Sheet

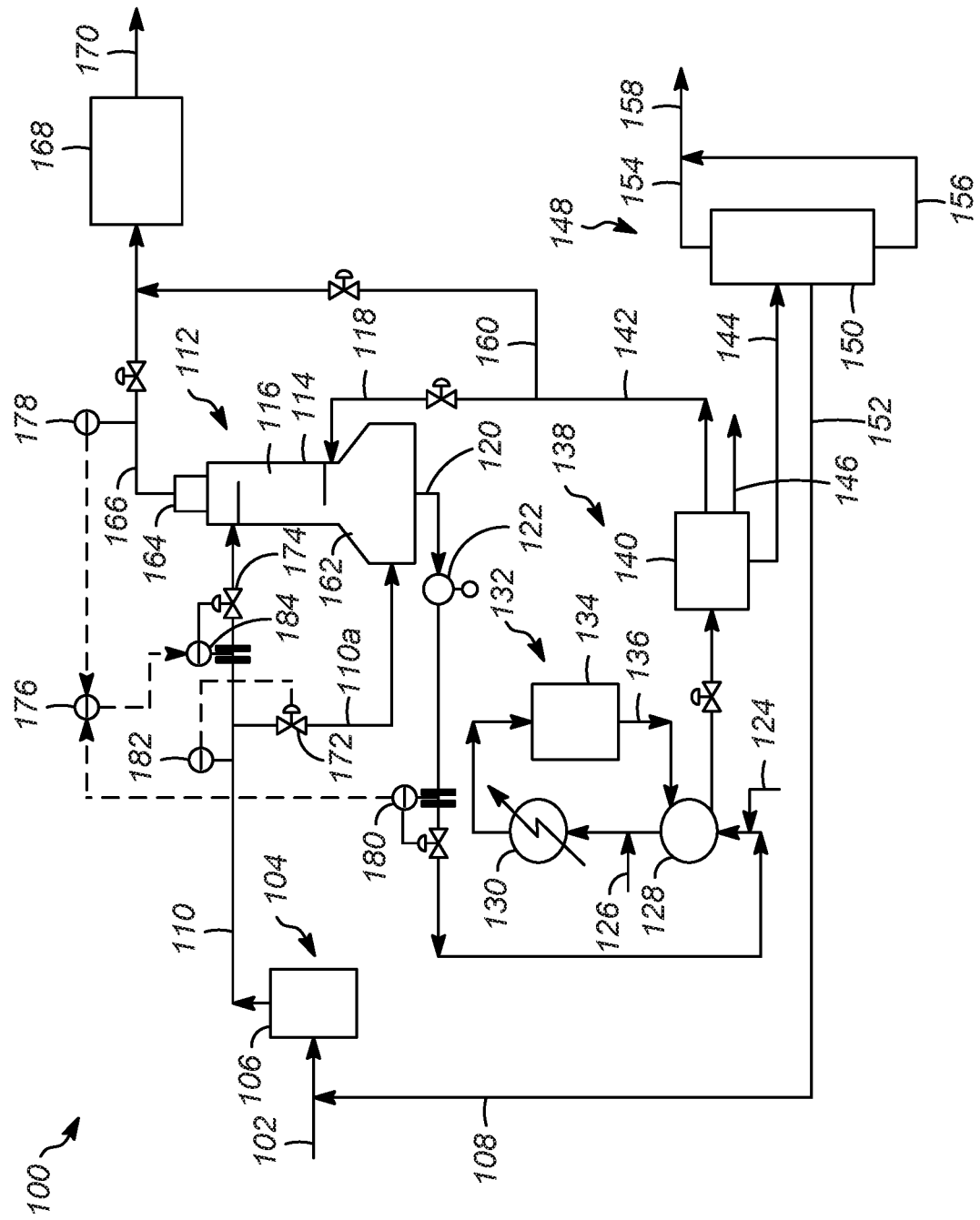

PROCESSES FOR ISOMERIZING HYDROCARBONS

FIELD OF THE INVENTION

The subject matter of the present disclosure generally relates to processes and apparatuses for isomerizing hydrocarbons, and more particularly relates to minimizing chloride and caustic consumption in such processes and apparatuses.

BACKGROUND OF THE INVENTION

Isomerization catalyst requires a continuous injection of chlorides to maintain the acid sites activity at a rate of 150 wppm of combined feed to isomerization reactors such as in UOP PENEX™ processes. The chlorides injected to the isomerization reactors result in the presence of hydrogen chloride and/or other chlorinated compounds in the gaseous and liquid effluents obtained from the isomerization unit. As is known in the art, these compounds inevitably lead to the corrosion of the facilities, formation of deposits or salts based on chlorine, and/or accelerate contamination of catalysts which might be located downstream of the isomerization unit. Thus, it is important to eliminate all traces of hydrogen chloride or other chlorinated compounds from these effluents.

Typically, such chlorides are scrubbed with a caustic solution in a net gas scrubber (NGS) before sending off gases to a fuel gas header or alternate destinations. This requires large amounts of caustic consumption on a continuous basis and refiners want to reduce the treatment cost of spent caustic. Caustic handling and treatment is an environmental concern and is cost intensive.

It is desirable to provide improved processes and apparatus for efficiently handling the chlorine injected into the isomerization process and reducing net chloride consumption. Further, it is desirable to reduce caustic consumption in the overall process, thereby decreasing associated costs.

Accordingly, the present Applicant, in U.S. patent application Ser. No. 15/813,057, filed Nov. 14, 2017 (the entirety of which is incorporated herein by refenced), provided processes and apparatuses which utilized an absorbing vessel for removing chlorides from the isomerized effluent with a portion of the isomerization feed stream.

While effective for its intended purposes, the disclosed processes used various pieces of equipment to chill or otherwise cool the feed stream before absorbing chlorides. Accordingly, it would be desirable to provide processes for absorbing chlorides from the isomerized effluent with a portion of the isomerization feed stream which do not require cooling or chilling equipment. Other desirable features and characteristics of the present subject matter will become apparent from the subsequent detailed description of the subject matter and the appended claims, taken in conjunction with the accompanying drawings and this background of the subject matter.

SUMMARY OF THE INVENTION

Various processes and apparatuses relating to isomerizing hydrocarbons and removing chlorides from the isomerized effluent have been invented. The exemplary embodiments taught herein minimize chloride and caustic consumption in processes and apparatus for isomerizing hydrocarbons. The disclosed processes recover the chlorides from stabilizer vapors and recycling it back to the isomerization reactor section to minimize the net chloride consumption and therefore minimize the caustic consumption. Furthermore, the present processes and apparatuses achieve the desired chloride levels without requiring equipment such as chillers and economizers.

Therefore, the present invention may be characterized, in at least one aspect, as providing a process for isomerizing a hydrocarbon feed stream comprising at least one of C4 to C7 hydrocarbons by: drying the hydrocarbon feed stream in a drying zone configured to remove water from the hydrocarbon feed stream and provide a dried hydrocarbon feed stream; absorbing chlorides from a gaseous stream with the dried hydrocarbon feed stream in a vessel having an absorbing section configured to provide a chloride rich hydrocarbon feed stream and a chloride lean vapor, wherein a temperature of the dried hydrocarbon feed stream at an inlet of the vessel is substantially equal to a temperature of the dried hydrocarbon feed stream at the drying zone; isomerizing the chloride rich hydrocarbon feed stream in the presence of an isomerization catalyst in an isomerization reaction zone under isomerization conditions to produce an isomerized effluent stream; and, stabilizing the isomerized effluent stream in a stabilizing zone to provide a stabilizer off-gas stream comprising chlorides and a liquid isomerate stream, wherein at least a portion of the stabilizer off-gas stream comprises the gaseous stream. An entirety of the dried hydrocarbon feed stream may be passed to the vessel. The process may include bypassing the absorbing section with a portion of dried hydrocarbon feed stream. The vessel may have a first section comprising the absorbing section and a second section which is a surge section. The first section may be disposed vertically above the second section. The vessel may further include a chiller disposed vertically above the first section having an operating temperature between −40 to 4° C. (−40 to 40° F.). The second section of the vessel may receive the portion of the dried hydrocarbon feed stream that bypasses the absorbing section. The portion of the dried hydrocarbon feed stream that bypasses the absorbing section may be between 5 to 40% (by volume) of the dried hydrocarbon feed stream. The process may include monitoring a chloride level of the chloride lean vapor and, adjusting the ratio of the portion of the dried hydrocarbon feed stream that bypasses the absorbing section to an amount of the dried hydrocarbon feed stream passed to the absorbing section based on the chloride level of the chloride lean vapor. The absorbing section may receive between 60 to 100% (by volume) of the dried hydrocarbon feed stream.

According to other aspects of the present invention, the present invention may also be characterized as providing a process for isomerizing a hydrocarbon feed stream that has at least one of $C_4$ to $C_7$ hydrocarbons by: drying the hydrocarbon feed stream in a drying zone configured to remove water from the hydrocarbon feed stream and provide a dried hydrocarbon feed stream; absorbing chlorides from a gaseous stream with the dried hydrocarbon feed stream in a vessel having an absorbing section configured to provide a chloride rich hydrocarbon feed stream and a chloride lean vapor; isomerizing the chloride rich hydrocarbon feed stream in the presence of an isomerization catalyst in an isomerization reaction zone under isomerization conditions to produce an isomerized effluent stream; stabilizing the isomerized effluent stream in a stabilizing zone to provide a stabilizer off-gas stream which includes chlorides and a liquid isomerate stream, wherein at least a portion of the stabilizer off-gas stream comprises the gaseous stream; and, cooling the chloride lean vapor in a chiller disposed on the vessel to provide a chilled chloride lean vapor stream. An entirety of the dried hydrocarbon feed stream may be passed to the vessel. The process may include bypassing the absorbing section with a portion of dried hydrocarbon feed stream. The vessel may have a first section that is the absorbing section and a second section that is a surge section. The first section may be disposed, or positioned, vertically above the second section, and the chiller may be disposed vertically above the first section. The second section of the vessel may receive the portion of the dried hydrocarbon feed stream that bypasses the absorbing section. The portion of the dried hydrocarbon feed stream that bypasses the absorbing section may be between 5 to 40% (by volume) of the dried hydrocarbon feed stream. The absorbing section may receive between 60 to 100% (by volume) of the dried hydrocarbon feed stream. A temperature of the dried hydrocarbon feed stream at an inlet of the vessel may be substantially equal to a temperature of the dried hydrocarbon feed stream at the drying zone.

According to some aspects, the present may also be characterized, generally, as providing an apparatus for isomerizing a hydrocarbon feed stream with at least one of $C_4$ to $C_7$ hydrocarbons. The apparatus may include: a drying zone configured to remove water from the hydrocarbon feed stream and provide a dried hydrocarbon feed stream; a vessel configured to receive the dried hydrocarbon feed stream and a gaseous stream with chlorides and provide a chloride rich hydrocarbon feed stream and a chloride lean vapor; an isomerization reaction zone having a reactor configured to receive the chloride rich hydrocarbon feed stream and, under isomerization conditions, provide an isomerized effluent stream; a stabilizing zone having a stabilizing column configured to receive and separate the isomerized effluent stream into a stabilizer off-gas stream with chlorides and a liquid isomerate stream, at least a portion of the stabilizer off-gas stream makes up the gaseous stream; and, a chiller configured to cool the chloride lean vapor of the vessel and provide a chilled chloride lean vapor stream.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing FIGURE, in which:

the FIGURE depicts a schematic diagram of a process and an apparatus for isomerizing hydrocarbons in accordance with an exemplary embodiment.

DETAILED DESCRIPTION OF THE INVENTION

As mentioned above, processes and apparatus for isomerizing hydrocarbons are provided herein. The processes include isomerizing at least a portion of a hydrocarbon feed stream comprising at least one of C4 to C7 hydrocarbons in the presence of an isomerization catalyst and hydrogen under isomerization conditions to produce an isomerized stream. The isomerized stream is stabilized in a stabilizer to provide a stabilizer off-gas stream comprising chlorides and a liquid isomerate stream. At least a portion of the stabilizer off-gas stream is contacted with a dried feed stream to remove chlorides from the stabilizer off-gas stream. The dried feed stream is not cooled before absorbing the chlorides. A portion of the dried feed stream may bypass the absorbing section. A chiller is disposed on top of the vessel with the absorbing section. An absorber bottoms stream is passed to the isomerization reactor.

As depicted, process flow lines in the FIGURE can be referred to, interchangeably, as, e.g., lines, pipes, branches, distributors, streams, effluents, feeds, products, portions, catalysts, withdrawals, recycles, suctions, discharges, and caustics.

As used herein, the term "unit" or "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "vapor" can mean a gas or a dispersion that may include or consist of one or more hydrocarbons.

As used herein, the term "stream" can include various hydrocarbon molecules and other substances. Moreover, the term "stream comprising Cx hydrocarbons" can include a stream comprising hydrocarbon with "x" number of carbon atoms, suitably a stream with a majority of hydrocarbons with "x" number of carbon atoms and preferably a stream with at least 75 wt % hydrocarbon molecules, respectively, with "x" number of carbon atoms. Moreover, the term "stream comprising Cx+ hydrocarbons" can include a stream comprising a majority of hydrocarbon molecules, with more than or equal to "x" carbon atoms and suitably less than 10 wt % and preferably less than 1 wt % hydrocarbon molecules, with x−1 carbon atoms. Lastly, the term "Cx− stream" can include a stream comprising a majority of hydrocarbon molecules with less than or equal to "x" carbon atoms and suitably less than 10 wt % and preferably less than 1 wt % hydrocarbon molecules, with x+1 carbon atoms.

As used herein, the term "overhead stream" can mean a stream withdrawn at or near a top of a vessel, such as a column.

The term "column" means a distillation column or columns for separating one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "bottoms stream" can mean a stream withdrawn at or near a bottom of a vessel, such as a column.

As used herein, the term "substantially" can mean an amount of generally at least about 90%, preferably about 95%, and optimally about 99%, by mole, of a compound or class of compounds in a stream.

With these general principles in mind, one or more embodiments of the present invention will be described with the understanding that the following description is not intended to be limiting.

An exemplary embodiment of the process and apparatus for isomerizing hydrocarbons is addressed with reference to a process and apparatus 100 according to an embodiment as shown in the FIGURE.

In accordance with an exemplary embodiment as shown in the FIGURE, a hydrocarbon feed stream 102 may be passed to a drying zone 104 which includes, for example, the drier 106. Drying is generally carried out in the drier 106 by adsorption over a molecular sieve which removes water from the hydrocarbon feed stream 102. A recycle stream 108 (discussed below) may also be mixed to the hydrocarbon feed stream 102 prior to being passed to the drying zone 104.

The hydrocarbon feed stream 102 includes at least one of C4 to C7 hydrocarbons. In one embodiment, the hydrocarbon feed stream 102 may be predominantly C5 and C6 hydrocarbons. In another embodiment, the hydrocarbon feed stream 102 may be predominantly C4 hydrocarbons. In yet another embodiment, the hydrocarbon feed stream 102 may be predominantly C7 hydrocarbons. In still another embodiment, the hydrocarbon feed stream 102 may include C5, C6, and C7 hydrocarbons. For the purposes of discussion of the instant embodiment, the hydrocarbon feed stream 102 is predominantly C5 and C6 hydrocarbons; however certain features are discussed in which the hydrocarbon feed stream 102 is predominantly C4 hydrocarbons.

At least a portion of the dried hydrocarbon feed stream 110 is passed from the drying zone 104 to an absorbing zone 112 which includes a vessel 114 having an absorbing section 116. A temperature of the dried hydrocarbon feed stream 110 at an inlet of the vessel 114 is substantially equal to a temperature of the dried hydrocarbon feed stream 110 at the drying zone 104. In other words, the temperature of the dried hydrocarbon feed stream 110 is not intentionally lowered with a chiller, heat exchanger, cooler, or other equipment; however, it is understood that the temperature of the dried hydrocarbon feed stream 110 can change due to heat losses to the environment. In the absorbing section 116, the dried hydrocarbon feed stream 110 absorbs chlorides from a gaseous stream 118. The absorbing zone 112 and the vessel 114 are discussed in more detail below.

In the FIGURE, a chloride rich hydrocarbon feed stream 120 may be passed through charge pumps 122. As shown, a make-up hydrogen gas 124 and a chloride compound 126 such as hydrogen chloride or perchloroethylene may be introduced to the chloride rich hydrocarbon feed stream 120, and the chloride rich hydrocarbon feed stream 120 may be heated in one or more heat exchangers 128, 130 before being passed to an isomerization reaction zone 132 having at least one reactor 134. The reactor 134 includes a suitable isomerization catalyst and is operated under isomerization conditions suitable to isomerize hydrocarbons from the chloride rich hydrocarbon feed stream 120 and provide an isomerized effluent 136.

The isomerized effluent 136 may be used to heat the chloride rich hydrocarbon feed stream 120 in a heat exchanger 128 and then is passed to a stabilizing zone 138 having a stabilizer unit 140. Separation of the isomerized effluent 136 is carried out in the stabilizer unit 140 to provide a stabilizer off-gas stream 142 comprising chlorides and a liquid isomerate stream 144. Further, an intermediate stream 146 comprising C3 and C4 hydrocarbons (LPG) may be withdrawn from the stabilizing zone 138 in order to reduce build-up of LPG in the apparatus 100.

The liquid isomerate 144 may be passed to a separation zone 148 including, for example, a deisohexanizer column 150 for separation. A deisohexanizer side draw stream 152 comprising linear hexane, cyclic hydrocarbons, and monomethyl-branched pentane may be withdrawn from the deisohexanizer column 150 and used as the recycle stream 108 combined with the hydrocarbon feed stream 102 (discussed above). The pentanes, dimethyl-butanes, and some monomethyl alkanes may be removed in a deisohexanizer overhead stream 154 and may be combined with the C6 naphthenes and C7+ in a deisohexanizer bottoms stream 156 to form an isomerate product stream 158.

Returning to the stabilizing zone 138, the stabilizer off-gas stream 142 comprises chlorides that are to be removed and recycled to the isomerization reaction zone 132. Accordingly, the stabilizer off-gas stream 142 or a portion thereof is passed to the vessel 114 of the absorbing zone 112 as the gaseous stream 118. A purge stabilizer off-gas stream 160, for example between 10 to 20% (by volume) may be removed and processed further which is discussed below.

As mentioned above, within the vessel 114 of the absorbing zone 112, the chloride compounds from the stabilizer off-gas stream 142 are absorbed by contact with the dried hydrocarbon feed stream 110 and returned to the isomerization reaction zone 132 in the chloride rich hydrocarbon feed stream 120. While prior processes and apparatuses used chilled feed streams for absorbing chlorides, the present disclosure provides for suitable chloride removal, in some instances up to 99.5%, by increasing the flow of the dried hydrocarbon feed stream 110 to the absorbing zone 112. TABLE 1, below, shows summary data from process simulations based on the principles of the present invention which indicates that the increased flow can achieve high levels of chloride recovery.

TABLE 1

C5 to C7 Absorber performance without feed chiller

| Liquid flow to Absorber | Absorber Operating Conditions | | Gas flow to Absorber | % HCl Recovery |
|---|---|---|---|---|
| (% of combined feed) | Pressure kPa (psig) | No. of Stages | (% of Stabilizer Off Gas) | across Absorber |
| 100% | 1241 (180) | 10 | 85% | 99.99% |
| 90% | 1241 (180) | 10 | 85% | 99.99% |
| 80% | 1241 (180) | 10 | 85% | 99.97% |
| 70% | 1241 (180) | 10 | 85% | 99.91% |
| 60% | 1241 (180) | 10 | 85% | 99.71% |
| 50% | 1241 (180) | 10 | 85% | 98.65% |
| 40% | 1241 (180) | 10 | 85% | 89.70% |
| 30% | 1241 (180) | 10 | 85% | 57.20% |
| 20% | 1241 (180) | 10 | 85% | 45.02% |
| 10% | 1241 (180) | 10 | 85% | 26.80% |
| 5% | 1241 (180) | 10 | 85% | 16.50% |
| 0% | 1241 (180) | 10 | 85% | 0.00% |

This increased flow allows for the same, or better, chloride removal without requiring the temperature reduction in prior processes. Thus, reducing equipment and operating costs.

Further, as shown above in TABLE 1, it may not be required to use the entirety of the dried hydrocarbon feed stream 110 in the absorbing zone 112. Accordingly, returning to the FIGURE, a portion 110a of the dried hydrocarbon feed stream 110 may bypass the absorbing section 116 of the absorbing zone 112. For example, the amount of the dried hydrocarbon feed stream 110 which bypasses the absorbing section 116 may be between 5 to 40%, or between 10 to 40%, or between 10 to 20% (by volume) of the dried hydrocarbon feed stream 110. Similarly, the amount of the dried hydrocarbon feed stream 110 which is passed to the absorbing section 116 may be between 60 to 100%, or between 70 to 90% (by volume) for a feed that is predominately C5 to C6 hydrocarbons. For a feed that is predominately C4 hydrocarbons, the amount of the dried hydrocarbon feed stream 110 which is passed to the absorbing section 116 may be between 10 to 40%, or between 15 to 25% (by volume).

In an embodiment, the vessel 114 of the absorbing zone 112 has a surge section 162 that is configured to receive the portion 110a of the dried hydrocarbon feed stream 110 that bypasses the absorbing section 116. The absorbing section 116 may be disposed on top of the surge section 162 so that both sections 116, 162 are in the same vessel 114, but the portion 110a of the dried hydrocarbon feed stream 110 that bypasses the absorbing section 116 will be introduced to the vessel 114 at a height that does not allow it to contact the stabilizer off-gas stream 142 within the vessel 114. The surge section 162 may have a greater diameter than the absorbing section 116. Bypassing the portion of dried feed directly to the surge section 162 of the vessel 114 allows for the reduction in size of the absorption section 116.

Furthermore, the vessel 114 may also include a chiller 164 mounted on the top of the absorbing section 116 of the vessel 114. The chiller 164 cools chloride lean vapor from the vessel 114 to remove C5+ hydrocarbon when the hydrocarbon feed stream 102 is predominantly C5 to C7 or C4+ hydrocarbon when feed is predominantly C4 carried over with vapor coming out of vessel 114 and provide a chilled chloride lean vapor stream 166. The chiller 164 may have an operating temperature of between about −40° C. (−40° F.) to 4° C. (40° F.). TABLE 2, below, shows summary data which indicates that the amount of C5+ hydrocarbon loss to stream 166 is reduced when operating temperature of chiller 164 is varied.

TABLE 2

Gaseous Stream from C5 to C7 Absorber Chiller Performance:

| | | | | |
|---|---|---|---|---|
| Liquid flow to Absorber (% of combined feed) | 100.0% | 100.0% | 100.0% | 100.0% |
| Absorber Operating Conditions | | | | |
| Liquid Feed Temp, ° C. (° F.) | 40 (104) | 40 (104) | 40 (104) | 40 (104) |
| Pressure kPa (psig) | 1241 (180) | 1241 (180) | 1241 (180) | 1241 (180) |
| Stages | 10 | 10 | 10 | 10 |
| Gas flow to Absorber (% of Stabilizer Off Gas) | 85.0% | 85.0% | 85.0% | 85.0% |
| % HCl Recovery Across Absorber | 99.99% | 99.99% | 99.99% | 99.99% |
| Absorber Overhead Chiller Outlet Temp, ° C. (° F.) | 40 (104) | 4.4 (40) | −17.8 (0) | −40 (−40) |
| C5+ loss in ABS Absorber gas | | | | |
| C5+ in Absorber overhead (lb/h) | 47.60 | 18.10 | 6.80 | 1.87 |
| Loss of feed to Absorber (wt %) | 0.168 | 0.041 | 0.014 | 0.004 |

The chilled chloride lean vapor stream 166 may be combined with the purge stabilizer off-gas stream 160 (discussed above) and passed to scrubbing zone 168 configured to remove any traces of chlorides and provide an off-gas stream 170 that is chloride free. While the scrubbing zone 168 may utilize caustic, it is significantly smaller as a result of the absorbing section 116. Alternatively, since the chloride content in the chilled chloride lean vapor stream 166 is reduced by 80 to 90% according to embodiments of the present processes, the scrubbing section 168 can also be replaced by chloride treaters which includes an adsorbent to remove the remaining traces of chlorides.

In order to adjust the flow of the dried hydrocarbon feed stream 110, including, the amount that bypasses the absorbing section 116, various valves 172, 174 may be adjusted by a controller 176. Signals, measurements, and/or data generated or recorded by monitoring components may be transmitted to one or more computing devices or systems, such as controller 176. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. For example, a chloride probe 178, or flow probes 180, 182, 184 may be in communication with the controller 176 to provide data for comparison and determining the need for adjustment (via associated valves) and/or the amount of the adjustment.

The present disclosure provides processes and apparatuses with greater reliability and improved stability across a wide range of unit throughput in achieved desired chloride recovery. It also allows for existing systems to be easily retrofitted, and requires less equipment than other configurations.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Specific Embodiments

While the following is described in conjunction with specific embodiments, it will be understood that this description is intended to illustrate and not limit the scope of the preceding description and the appended claims.

A first embodiment of the invention is a process for isomerizing a hydrocarbon feed stream comprising at least one of $C_4$ to $C_7$ hydrocarbons, the process comprising drying the hydrocarbon feed stream in a drying zone configured to remove water from the hydrocarbon feed stream and provide a dried hydrocarbon feed stream; absorbing chlorides from a gaseous stream with the dried hydrocarbon feed stream in a vessel comprising an absorbing section configured to provide a chloride rich hydrocarbon feed stream and a chloride lean vapor, wherein a temperature of the dried hydrocarbon feed stream at an inlet of the vessel is substantially equal to a temperature of the dried hydrocarbon feed stream at the drying zone; isomerizing the chloride rich hydrocarbon feed stream in the presence of an isomerization catalyst in an isomerization reaction zone under isomerization conditions to produce an isomerized effluent stream; and, stabilizing the isomerized effluent stream in a stabilizing zone to provide a stabilizer off-gas stream comprising chlorides and a liquid isomerate stream, wherein at least a portion of the stabilizer off-gas stream comprises the gaseous stream. An embodiment of the invention is one, any or all of prior embodiments in this paragraph up through the first embodiment in this paragraph wherein an entirety of the dried hydrocarbon feed stream is passed to the vessel. An embodiment of the invention is one, any or all of prior embodiments in this paragraph up through the first embodiment in this paragraph further comprising bypassing the absorbing section with a portion of dried hydrocarbon feed stream. An embodiment of the invention is one, any or all of prior embodiments in this paragraph up through the first embodiment in this paragraph wherein the vessel has a first section comprising the absorbing section and a second section comprising a surge section. An embodiment of the invention is one, any or all of prior embodiments in this paragraph up through the first embodiment in this paragraph wherein the first section is disposed vertically above the second section. An embodiment of the invention is one, any or all of prior embodiments in this paragraph up through the first embodiment in this paragraph wherein the vessel further comprises a chiller disposed vertically above the first section having an operating temperature between −40 to 4° C. (−40 to 40° F.). An embodiment of the invention is one, any or all of prior embodiments in this paragraph up through the first embodiment in this paragraph wherein the second section of the vessel receives the portion of the dried hydrocarbon feed stream that bypasses the absorbing section. An embodiment of the invention is one, any or all of prior embodiments in this paragraph up through the first embodiment in this paragraph wherein the portion of the dried hydrocarbon feed stream that bypasses the absorbing section comprises between 5 to 40% (by volume) of the dried hydrocarbon feed stream. An embodiment of the invention is one, any or all of prior embodiments in this paragraph up through the first embodiment in this paragraph further comprising monitoring a chloride level of the chloride lean vapor; and, adjusting the ratio of the portion of the dried hydrocarbon feed stream that bypasses the absorbing section to an amount of the dried hydrocarbon feed stream passed to the absorbing section based on the chloride level of the chloride lean vapor. An embodiment of the invention is one, any or all of prior embodiments in this paragraph up through the first embodiment in this paragraph wherein the absorbing section receives between 60 to 100% (by volume) of the dried hydrocarbon feed stream.

A second embodiment of the invention is a process for isomerizing a hydrocarbon feed stream comprising at least one of $C_4$ to $C_7$ hydrocarbons, the process comprising drying the hydrocarbon feed stream in a drying zone configured to remove water from the hydrocarbon feed stream and provide a dried hydrocarbon feed stream; absorbing chlorides from a gaseous stream with the dried hydrocarbon feed stream in a vessel having an absorbing section configured to provide a chloride rich hydrocarbon feed stream and a chloride lean vapor; isomerizing the chloride rich hydrocarbon feed stream in the presence of an isomerization catalyst in an isomerization reaction zone under isomerization conditions to produce an isomerized effluent stream; stabilizing the isomerized effluent stream in a stabilizing zone to provide a stabilizer off-gas stream comprising chlorides and a liquid isomerate stream, wherein at least a portion of the stabilizer off-gas stream comprises the gaseous stream; and, cooling the chloride lean vapor in a chiller disposed on the vessel to provide a chilled chloride lean vapor stream. An embodiment of the invention is one, any or all of prior embodiments in this paragraph up through the second embodiment in this paragraph wherein an entirety of the dried hydrocarbon feed stream is passed to the vessel. An embodiment of the invention is one, any or all of prior embodiments in this paragraph up through the second embodiment in this paragraph further comprising bypassing the absorbing section with a portion of dried hydrocarbon feed stream. An embodiment of the invention is one, any or all of prior embodiments in this paragraph up through the second embodiment in this paragraph wherein the vessel has a first section comprising the absorbing section and a second section comprising a surge section. An embodiment of the invention is one, any or all of prior embodiments in this paragraph up through the second embodiment in this paragraph wherein the first section is disposed vertically above the second section, and wherein the chiller is disposed vertically above the first section and has an operating temperature between −40 to 4° C. (−40 to 40° F.). An embodiment of the invention is one, any or all of prior embodiments in this paragraph up through the second embodiment in this paragraph wherein the second section of the vessel receives the portion of the dried hydrocarbon feed stream that bypasses the absorbing section. An embodiment of the invention is one, any or all of prior embodiments in this paragraph up through the second embodiment in this paragraph wherein the portion of the dried hydrocarbon feed stream that bypasses the absorbing section comprises between 5 to 40% (by volume) of the dried hydrocarbon feed stream. An embodiment of the invention is one, any or all of prior embodiments in this paragraph up through the second embodiment in this paragraph wherein the absorbing section receives between 60 to 100% (by volume) of the dried hydrocarbon feed stream. An embodiment of the invention is one, any or all of prior embodiments in this paragraph up through the second embodiment in this paragraph wherein a temperature of the dried hydrocarbon feed stream at an inlet of the vessel is substantially equal to a temperature of the dried hydrocarbon feed stream at the drying zone.

A third embodiment of the invention is an apparatus for isomerizing a hydrocarbon feed stream comprising at least one of $C_4$ to $C_7$ hydrocarbons, the apparatus comprising a drying zone configured to remove water from the hydrocarbon feed stream and provide a dried hydrocarbon feed stream; a vessel configured to receive the dried hydrocarbon feed stream and a gaseous stream comprising chlorides and provide a chloride rich hydrocarbon feed stream and a chloride lean vapor; an isomerization reaction zone having a reactor configured to receive the chloride rich hydrocarbon feed stream and, under isomerization conditions, provide an isomerized effluent stream; a stabilizing zone having a stabilizing column configured to receive and separate the isomerized effluent stream into a stabilizer off-gas stream comprising chlorides and a liquid isomerate stream, wherein at least a portion of the stabilizer off-gas stream comprises the gaseous stream; and, a chiller configured to cool the chloride lean vapor of the vessel and provide a chilled chloride lean vapor stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for isomerizing a hydrocarbon feed stream comprising at least one of C4 to C7 hydrocarbons, the process comprising:
   drying the hydrocarbon feed stream in a drying zone configured to remove water from the hydrocarbon feed stream and provide a dried hydrocarbon feed stream;
   absorbing chlorides from a gaseous stream with the dried hydrocarbon feed stream in a vessel comprising an absorbing section configured to provide a chloride rich hydrocarbon feed stream and a chloride lean vapor, wherein a temperature of the dried hydrocarbon feed stream at an inlet of the vessel is substantially equal to a temperature of the dried hydrocarbon feed stream at the drying zone;
   isomerizing the chloride rich hydrocarbon feed stream with an isomerization catalyst in an isomerization reaction zone under isomerization conditions to produce an isomerized effluent stream; and,
   stabilizing the isomerized effluent stream in a stabilizing zone to provide a stabilizer off-gas stream comprising chlorides and a liquid isomerate stream, wherein at least a portion of the stabilizer off-gas stream comprises the gaseous stream.

2. The process of claim 1 wherein an entirety of the dried hydrocarbon feed stream is passed to the vessel.

3. The process of claim 1 further comprising:
   bypassing the absorbing section with a portion of the dried hydrocarbon feed stream.

4. The process of claim 3 wherein the vessel has a first section comprising the absorbing section and a second section comprising a surge section.

5. The process of claim 4 wherein the first section is disposed vertically above the second section.

6. The process of claim 5 wherein the vessel further comprises a chiller disposed vertically above the first section having an operating temperature between −40 to 4° C. (−40 to 40° F.).

7. The process of claim 4 wherein the second section of the vessel receives the portion of the dried hydrocarbon feed stream that bypasses the absorbing section.

8. The process of claim 3 wherein the portion of the dried hydrocarbon feed stream that bypasses the absorbing section comprises between 5 to 40% (by volume) of the dried hydrocarbon feed stream.

9. The process of claim 3 further comprising:
   monitoring a chloride level of the chloride lean vapor; and,
   adjusting a ratio of the portion of the dried hydrocarbon feed stream that bypasses the absorbing section to an amount of the dried hydrocarbon feed stream passed to the absorbing section based on the chloride level of the chloride lean vapor.

10. The process of claim 1 wherein the absorbing section receives between 60 to 100% (by volume) of the dried hydrocarbon feed stream.

11. A process for isomerizing a hydrocarbon feed stream comprising at least one of C4 to C7 hydrocarbons, the process comprising:
    drying the hydrocarbon feed stream in a drying zone configured to remove water from the hydrocarbon feed stream and provide a dried hydrocarbon feed stream;
    absorbing chlorides from a gaseous stream with the dried hydrocarbon feed stream in a vessel having an absorbing section configured to provide a chloride rich hydrocarbon feed stream and a chloride lean vapor;
    isomerizing the chloride rich hydrocarbon feed stream with an isomerization catalyst in an isomerization reaction zone under isomerization conditions to produce an isomerized effluent stream;
    stabilizing the isomerized effluent stream in a stabilizing zone to provide a stabilizer off-gas stream comprising chlorides and a liquid isomerate stream, wherein at least a portion of the stabilizer off-gas stream comprises the gaseous stream; and,
    cooling the chloride lean vapor in a chiller disposed on the vessel to provide a chilled chloride lean vapor stream.

12. The process of claim 11 wherein an entirety of the dried hydrocarbon feed stream is passed to the vessel.

13. The process of claim 11 further comprising:
    bypassing the absorbing section with a portion of the dried hydrocarbon feed stream.

14. The process of claim 13 wherein the vessel has a first section comprising the absorbing section and a second section comprising a surge section.

15. The process of claim 14 wherein the first section is disposed vertically above the second section, and wherein the chiller is disposed vertically above the first section and has an operating temperature between −40 to 4° C. (−40 to 40° F.).

16. The process of claim 14 wherein the second section of the vessel receives the portion of the dried hydrocarbon feed stream that bypasses the absorbing section.

17. The process of claim 13 wherein the portion of the dried hydrocarbon feed stream that bypasses the absorbing section comprises between 5 to 40% (by volume) of the dried hydrocarbon feed stream.

18. The process of claim 11 wherein the absorbing section receives between 60 to 100% (by volume) of the dried hydrocarbon feed stream.

19. The process of claim 11 wherein a temperature of the dried hydrocarbon feed stream at an inlet of the vessel is substantially equal to a temperature of the dried hydrocarbon feed stream at the drying zone.

\* \* \* \* \*